(12) United States Patent
Coates

(10) Patent No.: US 8,834,441 B2
(45) Date of Patent: Sep. 16, 2014

(54) UNDERGARMENT WITH HIDDEN CORE POCKET WITH ISOLATING FLUID LAYER

(76) Inventor: Fredrica V. Coates, Winston-Salem, NC (US)

(*) Notice: Subject to any disclaimer, the term of this patent is extended or adjusted under 35 U.S.C. 154(b) by 285 days.

(21) Appl. No.: 13/510,303

(22) PCT Filed: Oct. 15, 2010

(86) PCT No.: PCT/US2010/052811
§ 371 (c)(1),
(2), (4) Date: Sep. 17, 2012

(87) PCT Pub. No.: WO2011/049827
PCT Pub. Date: Apr. 28, 2011

(65) Prior Publication Data
US 2013/0006210 A1    Jan. 3, 2013

Related U.S. Application Data

(60) Provisional application No. 61/279,294, filed on Oct. 19, 2009.

(51) Int. Cl.
*A61F 13/505* (2006.01)
*A61F 13/15* (2006.01)

(52) U.S. Cl.
USPC ............ 604/385.19; 604/378; 604/385.101; 604/380; 604/379

(58) Field of Classification Search
USPC ............ 604/378, 385.101, 380, 379, 385.19
See application file for complete search history.

(56) References Cited

U.S. PATENT DOCUMENTS

| | | | | |
|---|---|---|---|---|
| 5,360,422 A | * | 11/1994 | Brownlee et al. | ........ 604/385.15 |
| 5,772,649 A | * | 6/1998 | Siudzinski | .................... 604/386 |
| 2003/0199844 A1 | * | 10/2003 | LaVon et al. | ............. 604/385.14 |

* cited by examiner

*Primary Examiner* — Jacqueline F. Stephens
(74) *Attorney, Agent, or Firm* — Shumaker, Loop & Kendrick, LLP

(57) ABSTRACT

An undergarment, such as a diaper, includes a hidden central core pocket for receipt of an absorbent pad. The pocket is formed between an inner, fluid permeable layer and a fluid isolation layer. The fluid isolation layer is attached to the inner or anchor layer and is located between the inner layer and an outer layer to which the inner layer is attached. The pocket is narrower than the outer to isolate fluids from edges of the outer layer and from diaper leg openings. Both the fluid isolation layer and the outer layer may be fluid resistant to provide additional protection against leakage. Adjustment fasteners on the outside of the outer shell permit size adjustment for the diaper and the adjustment fasteners are positioned within the periphery of the pocket so that presence of the absorbent pad will enhance comfort.

14 Claims, 8 Drawing Sheets

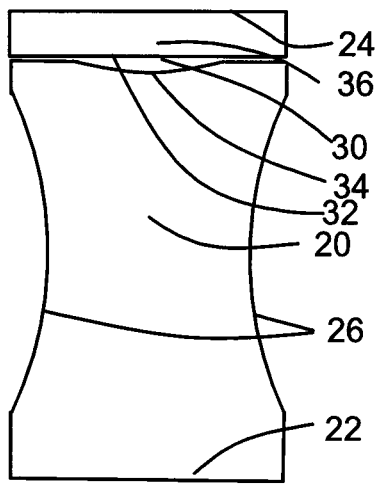
FIG 8A
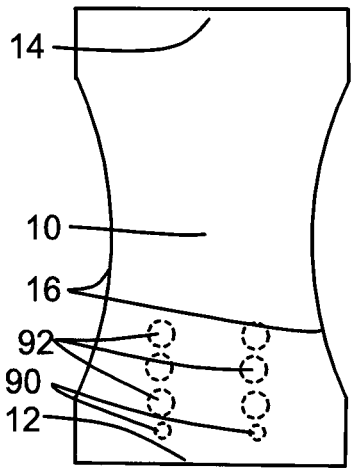
FIG 8B
FIG 8C
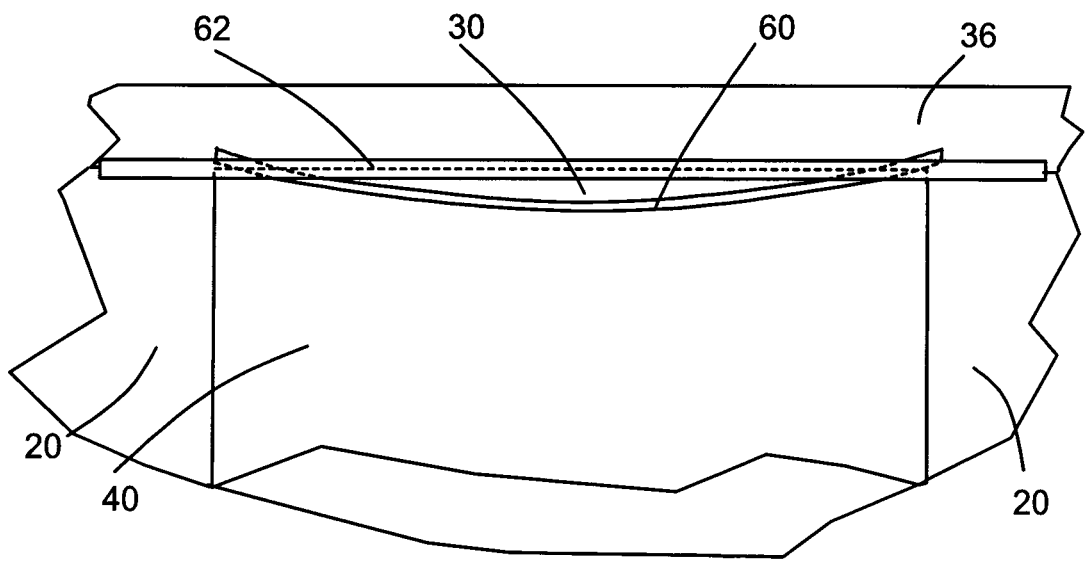
FIG 11

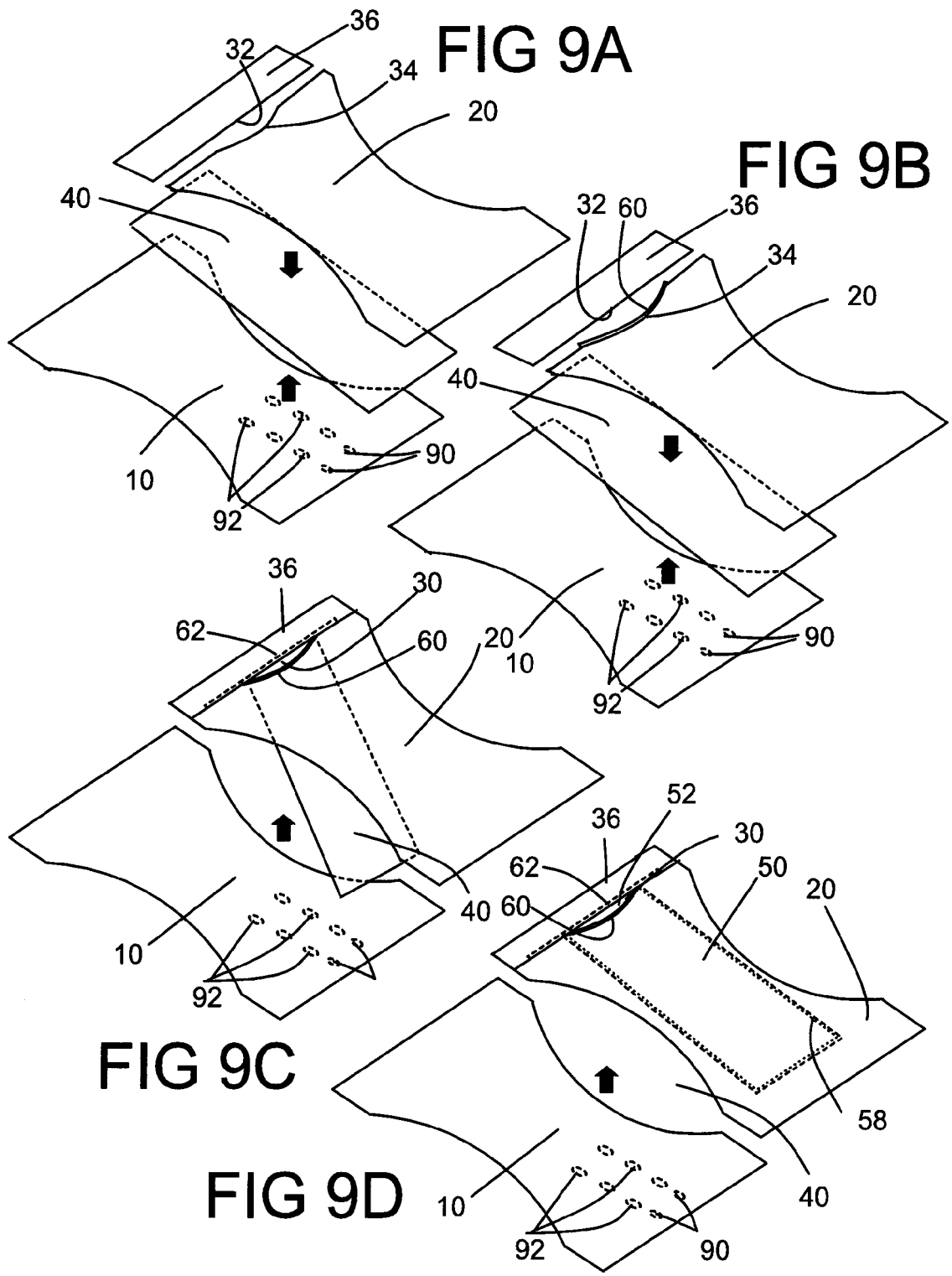

UNDERGARMENT WITH HIDDEN CORE POCKET WITH ISOLATING FLUID LAYER

BACKGROUND OF THE INVENTION

1. Field of the Invention

This invention relates to protective underwear, such as diapers, that can employ reusable absorbent pads. More specifically, this invention relates to a diaper having a pocket located between a fluid permeable inner layer and an outer layer.

2. Description of the Prior Art

Protective undergarments, such as diapers, employing reusable absorbent pads are employed as an alternative to disposable diapers. The absorbent pads can be positioned in slings, pockets or sleeve formed by other parts of these reusable protective undergarments. U.S. Pat. No. 5,707,364 shows several versions of such diapers, including versions employing a channel in which the absorbent pad is disposed between inner an outer layers with strips extending between these two layers forming the sides of the channel.

Some commercially available diapers employ a sleeve or channel that is stitched to an outer layer of the diaper. Others employ an intermediate layer inside of the outer layer, with the sleeve attached to this intermediate layer. The outer layer comprises a fluid resistant layer that comprises the primary fluid barrier to prevent leakage. Leakage can still remain a problem, with fluid leaking through stitches or through leg opening formed in the diaper. When these diapers are adjusted to fit individuals of different sizes, the legs openings need to tightly fit the wearer to prevent leakage through the leg openings.

The instant invention employs a fluid isolation layer to form the pocket so that the outer layer need not be the sole means of preventing leakage. Furthermore this can be achieved with a diaper in which the pocket fits between inner and outer layers, and in which discomfort due to adjustable fasteners can be reduced if not eliminated.

SUMMARY OF THE INVENTION

An undergarment, such as a diaper includes an outer layer, an inner layer, and a fluid isolation layer between the outer layer and the inner layer. The fluid isolation layer is joined to the inner layer to form a pocket, having a pocket opening on at least one end of the undergarment. The fluid isolation layer has a width less than a distance between opposite sides of the inner layer and outer layer forming leg opening when the garment is positioned on a wearer. The pocket is thus inwardly spaced and isolated from opposite sides of the undergarment leg openings. The inner layer may also include a slot located adjacent one end thereof. The slot in part forms a pocket opening between the inner layer and the fluid isolation layer.

Furthermore according to this invention, a diaper has an outer layer defining a diaper length extending between a rear and front end of the diaper. An inner layer is attached to the outer layer. A fluid isolation layer is located between the outer layer and the inner layer. The fluid isolation layer is joined to the inner layer to form a pocket for receipt of an absorbent pad. The pocket having a pocket opening on at least one end of the undergarment, wherein the fluid isolation layer has a width less than the outer layer. Mutually engagable and disengagable length adjustment fasteners are arranged in at least three rows and attached to the outer layer. The length of the diaper between the rear and front end of the diaper can be adjusted by engagement of adjustment fasteners in different rows so that the diaper can be adjusted to fit wearers of different sizes. The pocket extends beyond the rows of adjustment fasteners so that the absorbent pad will be positioned between the adjustment fasteners and the wearer for the wearer's comfort.

BRIEF DESCRIPTION OF THE DRAWINGS

FIG. 8A shows a moisture permeable, skin friendly inner layer prior to assembly. FIG. 8B shows the fluid isolation layer prior to attachment to the moisture permeable inner layer shown in FIG. 8A. FIG. 8C shows the outer layer, which can be either fluid resistant or fluid absorbent.

FIGS. 9A-9D shows four steps in the construction of the pocket. FIG. 9A shows four flat components that are employed to construct the diaper. FIG. 9B shows the addition of a front elastic strip on the lower edge of the slot at the top of the inner layer. FIG. 9C shows the attachment strip joined to the top of the inner layer and the addition of the rear elastic strip. FIG. 9D shows the attachment of the fluid isolation layer to the inner layer to form the hidden core pocket with the slot between the attachment strip and the inner layer now becoming a pocket opening, surrounded on front and back by elastic.

FIG. 10A shows elastic secured around a slot that will become the hidden pocket opening. FIG. 10B shows the fluid isolation layer stitched to the fluid permeable inner or anchor layer with the outer layer positioned behind the inner layer and the hidden pocket. FIG. 10C shows the addition of the outer layer to the subassembly of FIG. 10B, with elastic being stitched around the leg holes formed by the inner layer and the outer layer. FIG. 10D shows the addition of fasteners to the subassembly of FIG. 10C.

FIG. 11 is a partial view of the surfaces of the inner layer and the fluid isolation layer that will be hidden upon completion of fabrication of the undergarment, and shows the manner in which a rear elastic strip is attached so that elastic will surround the slot that will eventually form the pocket opening, with the rear elastic between the fluid isolation layer and the inner layer where it cannot pinch the wearer's skin.

DETAILED DESCRIPTION OF THE PREFERRED EMBODIMENT

Figure 1:
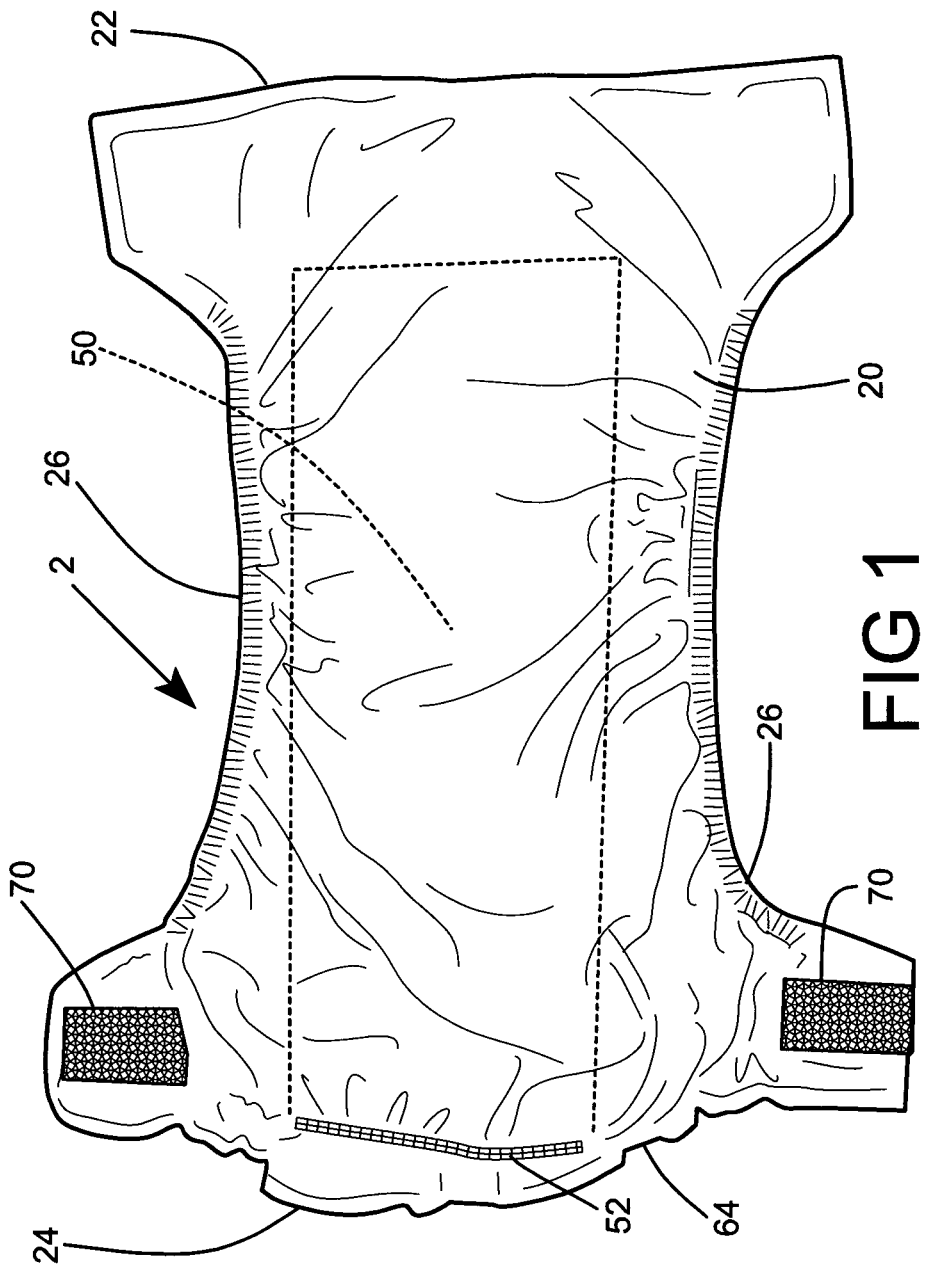
FIG. 1 is a view of the undergarment, shown in the form of a diaper, with a fluid permeable inner layer exposed and with the pocket entrance being located at the rear end of the undergarment.
Figure 2:
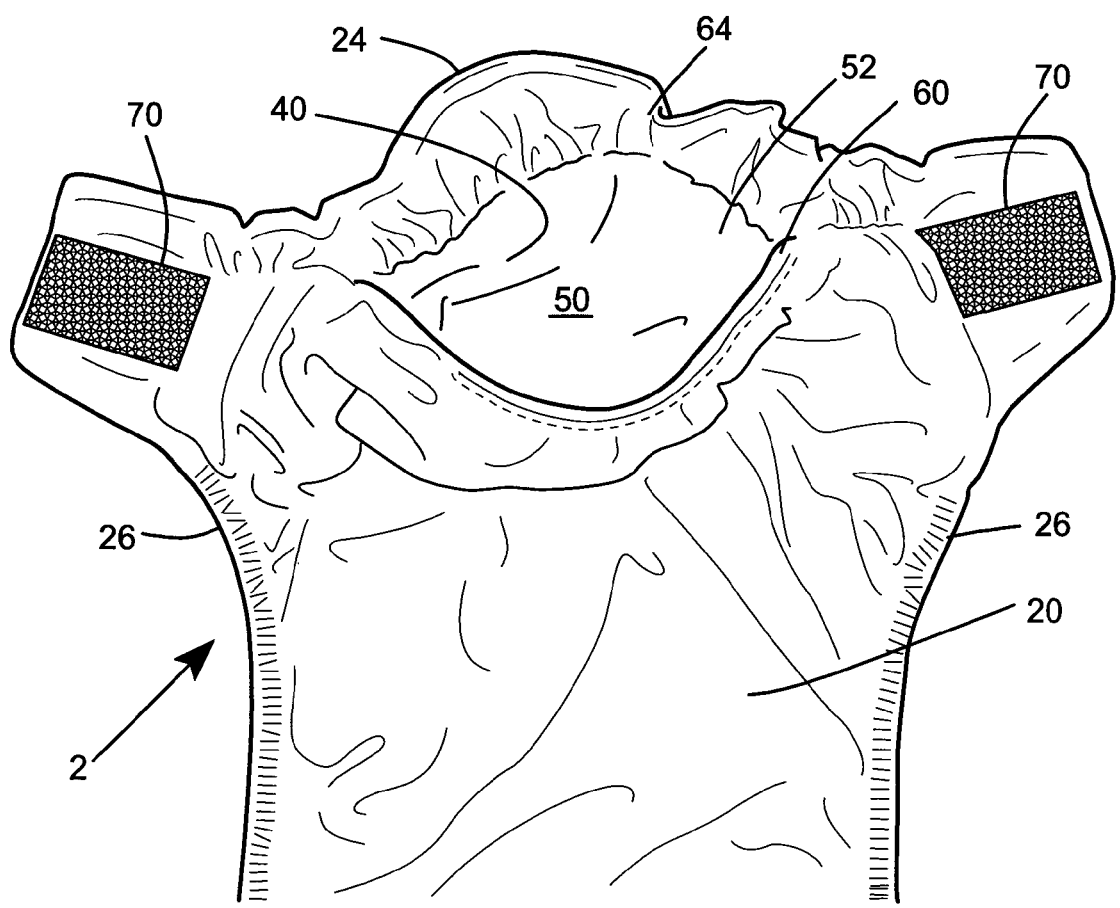
FIG. 2 is a view of the rear end of the undergarment with the pocket entrance show in an open position.
Figure 3:
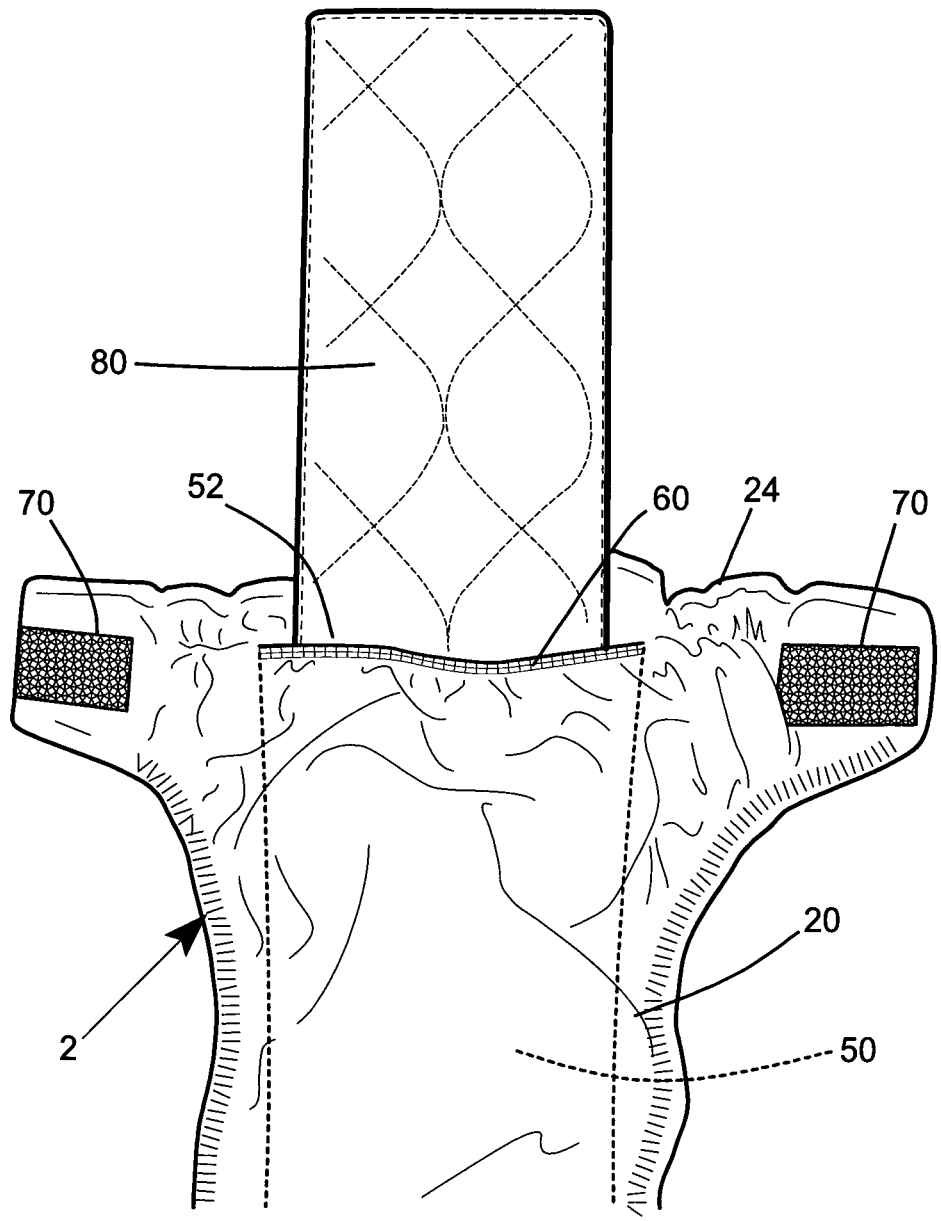
FIG. 3 is a view showing how an absorbent pad can be inserted into and removed from the pocket.
Figure 4:
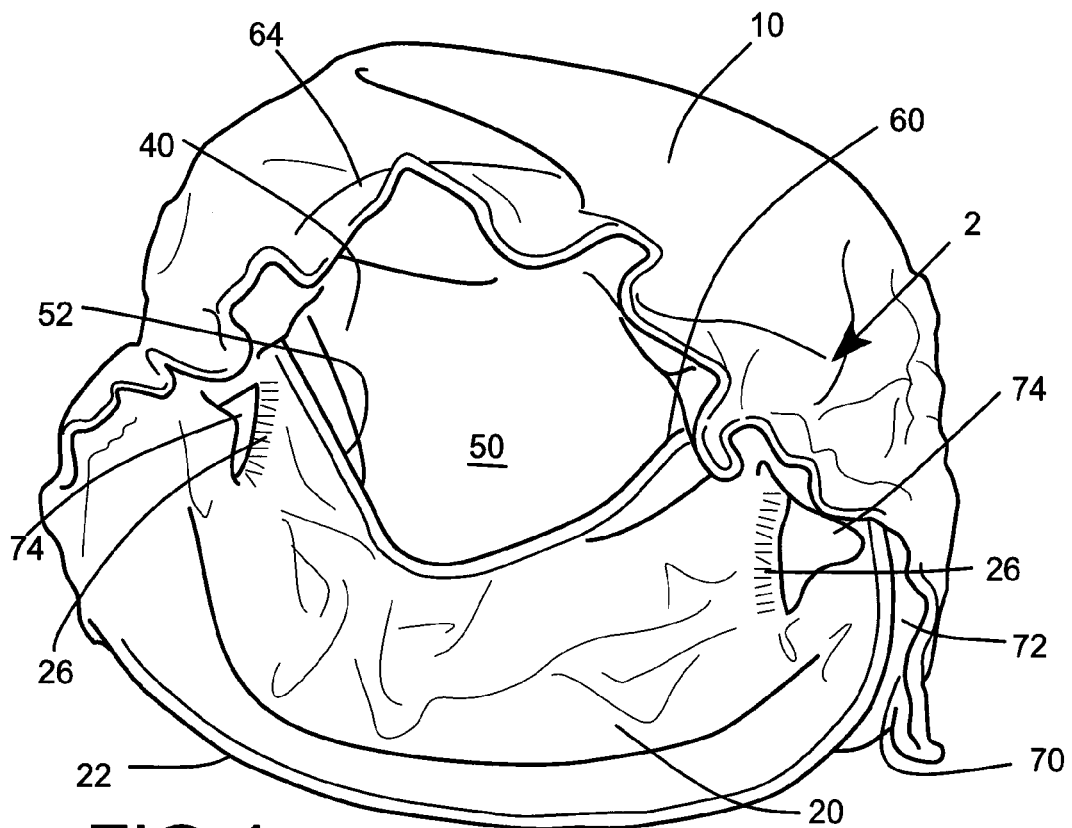
FIG. 4 is a view showing how the undergarment, in the form of a diaper, will be secured to surround the wearer. The open pocket can also be seen.
Figure 5:
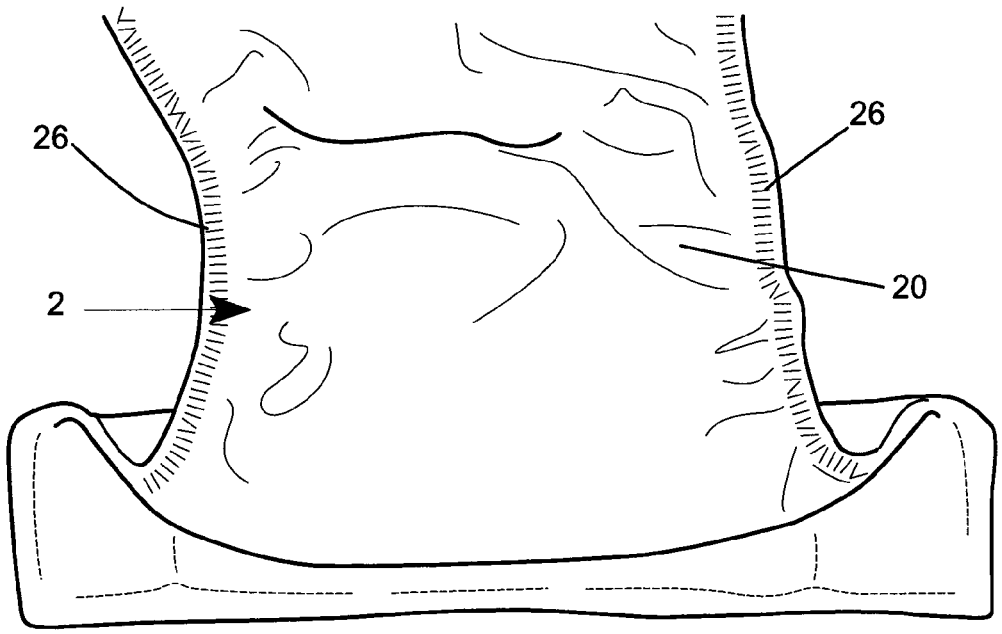
FIG. 5 is a view showing one manner of adjusting the size of a diaper, so that one version of the diaper can be adjusted to different sizes.
Figure 6:
FIG. 6 is a view of the undergarment of FIGS. 1-6 in which the undergarment has been turned inside out to show the moisture permeable inner layer.
Figure 7:
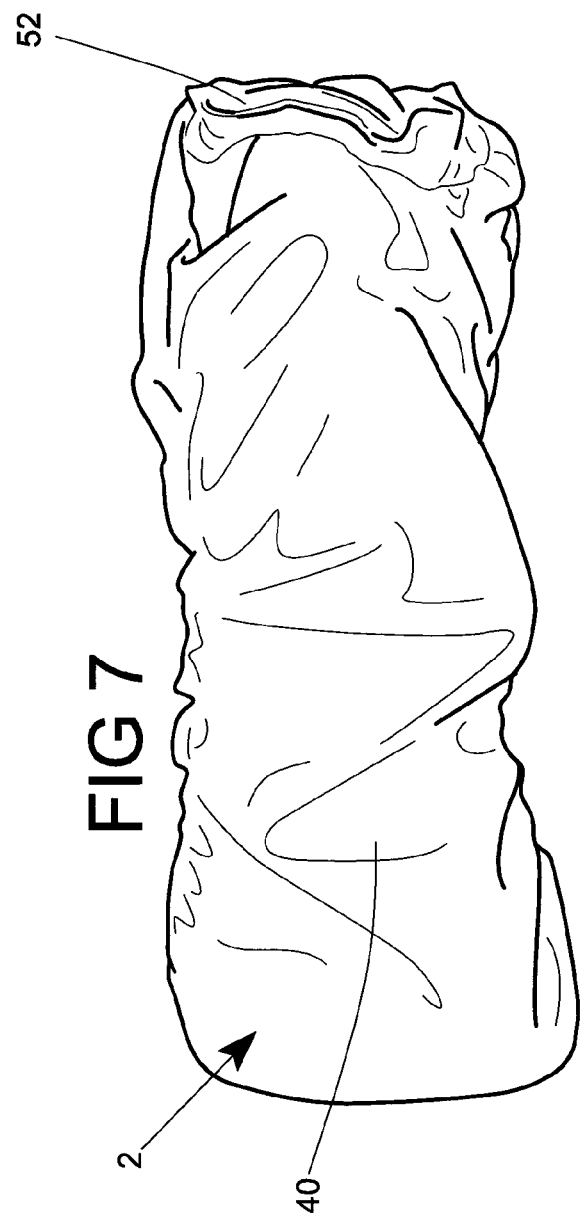
FIG. 7 is a view of the undergarment of FIGS. 1-6 that is similar to that shown in FIG. 6, but shows the fluid isolation layer which forms the outside of the pocket.
Figure 10A:
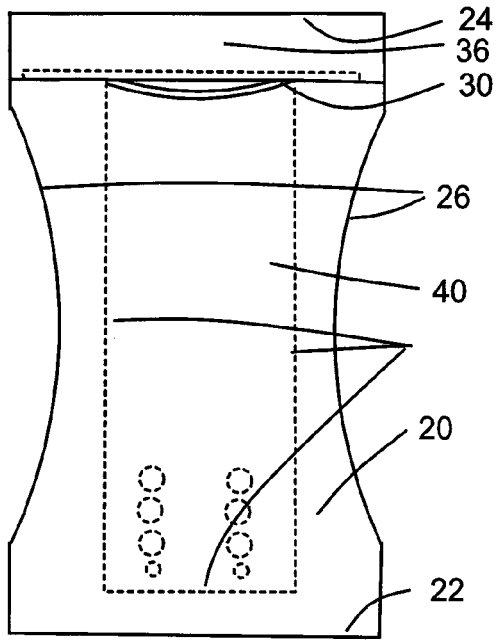
FIGS. 10A-10D shows the orientation of the components when viewed from and inside surface and demonstrating some of the diaper fabrication steps.
Figure 10B:
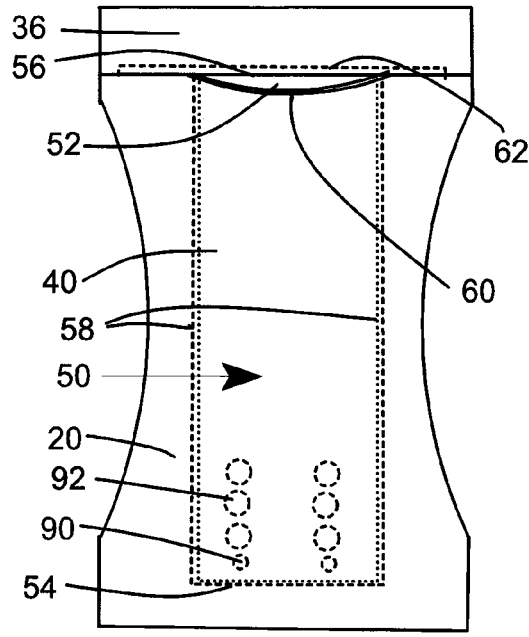
Figure 10C:
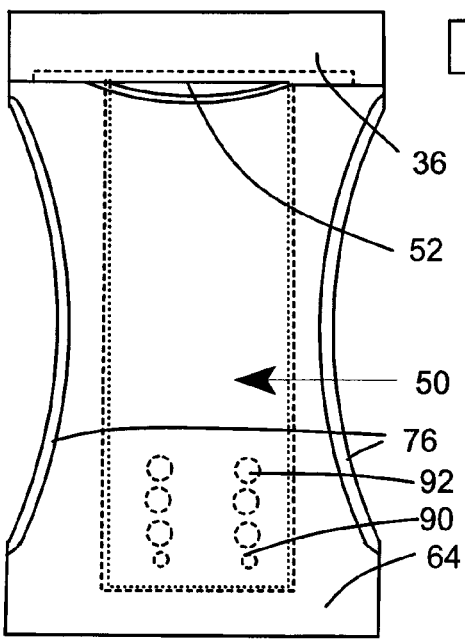
Figure 10D:
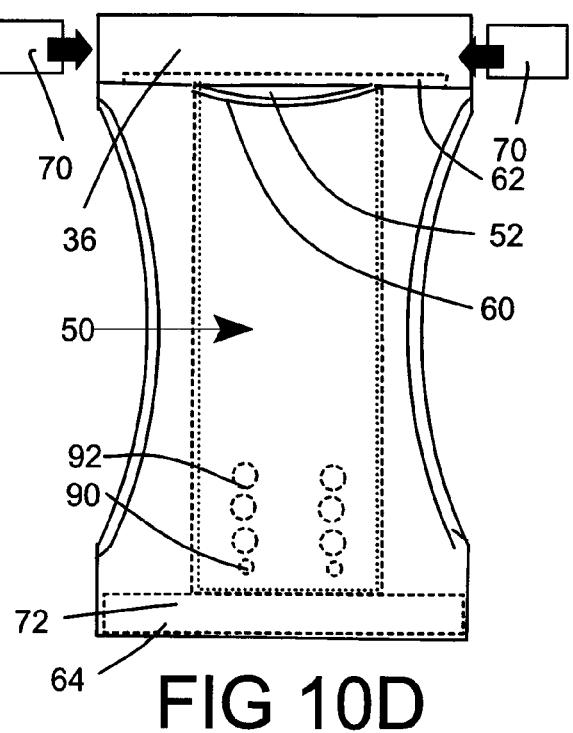

FIGS. 1-7 are views of an undergarment 2. The preferred embodiment of the undergarment 2 is in the form of a diaper 2. FIGS. 8A-8C, 9A-9B and FIGS. 10A-10D are views showing the components of the diaper embodiment and its construction. It should be understood, however that this invention is not limited to the diaper embodiment.

The undergarment 2 is reusable and is intended for use with a reusable and washable fluid absorbent pad 80 that can be inserted into and removed from a hidden central core pocket 50. Disposable pads could also be employed. Undergarment 2 is a protective undergarment in that it will prevent leakage of fluids from the absorbent pad 80 to the environment as well as adding protection the wearer from excessive wetness.

The undergarment 2 includes an outer layer 10, an inner or anchor layer 20 and an intermediate fluid isolation layer 40 between the outer layer 10 and the inner layer or anchor liner 20. In the preferred embodiment the outer layer 10 will be fabricated from a fluid resistant material that will prevent fluid leakage over most of the surface of the protective undergarment or diaper 2. The inner layer or anchor liner 20 is preferably fabricated from a fluid permeable, skin friendly material, such as a fleece material. Fluids excreted by the wearer will penetrate and flow through this permeable inner layer 20, and will be absorbed in the fluid absorbent pad 80 positioned within the hidden central core pocket 50.

The hidden central core pocket 50 is formed between the inner layer 20 and a fluid isolation layer 40, which is attached, and preferably stitched, directly to the inner layer 20 so that the inner layer 20 serves as an anchor layer or liner supporting the fluid isolation layer 40. The fluid isolation layer 40 can be fabricated from the same fluid or moisture resistant or fluid impermeable material as the outer layer 10. This fluid isolation layer 40 will not only provide fluid resistance in addition to that provided by the outer layer 10, but will also retard leakage past stitches or other porous areas on the outer layer 10, as well as leakage through and around elasticized leg openings 74. Since most, if not all fluids will not reach areas, such as the leg openings 74, the fluid isolation layer 40 and the pocket 50 partially formed thereby can be considered to be the primary fluid bather for this undergarment. Although the outer layer 10 will normally be fabricated from a fluid resistant material, the presence of the fluid isolation layer 40 will allow the use of a fluid absorbent material in the outer layer 10 for decoration, tactile or other purposes.

Except along the rear end, the outer layer 10 and the inner layer 20 have the same general peripheral shape, and these two layers will attached to each other around their peripheries, by conventional stitching or seams. The outer layer 10 has a front end 12 and a rear end 14 with curved opposite sides 16 extending between the front end 12 and the rear end 14. The inner layer 20 also has an inner layer front end 22 that will be joined to the outer layer front end 12. A fabric attachment strip or bar 36 is first joined to the rear end 24 of the inner or anchor layer 20 before joining the two exposed layers 10 and 20 around peripheral edges including the peripheral edges of the strip or bar 36. Opposite curved sides 16 of the outer layer 10 will be joined to inner layer curved sides 26 when the inner layer 20 is peripherally attached or stitched to the outer layer 10 when these two layers are positioned in overlapping relationship. Although the shape of the outer layer 10 and the inner layer 20, including the attachment bar 36, are substantially the same, it should be understood that these two layers 10 and 20 will normally be fabricated from different materials.

Other that being fabricated from different materials, the main difference between the inner layer 20 and the outer layer 10 is the presence of a slot 30 at the rear end 24 of the inner layer 20, between the inner layer 20 and the attachment bar 36. Slot 30 is formed between an end of the inner layer 20 and the attachment bar 36. A notch with a lower curved edge 34 is formed at the end of the inner layer and this notch forms lower slot edge 34. When the attachment strip or bar 36 is attached to the inner layer 20, the upper slot edge 32 will be defined by a lower edge of the attachment bar 36. Slot 30 is spaced from the outer edge of the rear end 24 and in the preferred embodiment will be generally parallel to this outer edge. The slot 30 does not extend between opposite sides of the inner layer 20, but terminates so that the length of the slot 30 will be less than the spacing between the curved opposite sides 26 of the inner layer. Since the slot 30 will form a portion of the opening or entrance 52 to the pocket 50 when fabrication of the undergarment is complete, the width of this pocket must be less than the spacing between opposite sides of the inner layer 26 and the entire undergarment 2.

The fluid isolation layer 40 will be stitched to the inner layer 20 to form opposite sides of the pocket 50. In the preferred embodiment layers 20 and 40 will be positioned in overlapping relationship and will initially form two flat layers without the need for additional side portions extending transversely to the layers 20 and 40. This will reduce the bulk of the overall construction. As shown in FIGS. 8A-8C, the fluid isolation layer 40 is generally rectangular and has a width that is less than the minimum width of both the outer layer 10 and the inner layer 20. The length of the fluid isolation layer 40 will also be less than the distance between the respective front and rear edges of the outer layer 10 and the inner layer 20. These dimensions are dictated in the preferred embodiment because the outer dimensions of the pocket 50 will conform to the outer dimensions of the fluid isolation layer 40. It should be understood, however, that in other embodiments, the fluid isolation layer 40 can have the same dimensions and shape as the outer layer 10 and the inner layer 20, with the pocket 50 being formed by stitching the fluid isolation layer 40 to the inner layer 20 along lines spaced inwardly form the outer edges of both pieces of material. However, in most circumstances, this alternate embodiment would result in the waste of material and the addition of bulk to the completed undergarment 2.

In the preferred method of fabricating the pocket 50 the top side of the fluid isolation layer 40 is joined, attached or stitched along the center of the isolation bar 36 as shown in FIGS. 9C, and 10A, 10B and FIG. 11, after which the attachment bar or strip 36 is joined to the adjacent edge of the inner or anchor layer 20. The fluid isolation layer top edge 44 is positioned on the surface of the attachment bar or strip 36 that will eventually face away from the wearer where it will be stitched to the slot upper edge 32 on the attachment bar 36. The remainder of the fluid isolation layer 40 defining the pocket 50 is then stitched or attached to the face of the inner layer 20 that will face away from the wearer along pocket stitches 58 that will extend along the opposite sides 46 and the bottom side 42 of the pocket. This will form a pocket opening 52 near, but spaced from the rear end of the undergarment 2. The upper slot edge 32 will extend along the rear of the pocket entrance or opening 52 and the lower slot edge 34 will extend along the front of the pocket entrance or opening 52.

Before the fluid isolation layer top edge 44 is sewn to the upper slot edge 32, on the attachment strip 36, front elastic 60 will be sewn over front edge of the notch on the inner layer 20 as shown in FIG. 9B. The front elastic 60 will be located the front of the pocket entrance 52. A rear elastic 62 will be sewn along the edge of the attachment bar 36 forming the remainder of the slot entrance or opening 52. See FIGS. 9C and 11. FIG. 11 shows the manner of attaching this rear elastic 62 to both the attachment bar or strip 36 and the inner layer 20. After the attachment strip or bar 36 has been stitched to the rearmost edge of the inner layer 20 the fluid isolation layer 40 will be placed in position between opposite sides of the inner layer 22. Small opening may be left in the stitching between the attachment strip 36 and the inner layer 20, to provide room for ends of the front elastic strip 60 that may extend beyond the opposite sides of the rectangular fluid isolation layer 40. The rear elastic strip 62 will then be stitched over a seam between the attachment strip 36 and the inner layer 20, as well as end sections of the front elastic 60. Elastic will then extend along both the top and bottom edges of the slot 30 where elastic will surround the pocket opening 50 that will be formed by slot 30. The views showing the elastic strips 60 and 60 show them, as well as the surrounding material as being flat. It should be understood of course that with the elastic strips in their neutral position, they will tend to draw the surrounding fabric together. When an absorbent pad 80 is inserted into pocket 50, the elastic will expand, and perhaps more importantly front and rear elastic strips 60 and 62 will expand. This expansion will cause the lower curved elastic edge 60 to straighten out and move toward the top elasticized edge of the pocket 50. This will restrict the size of the pocket opening 52 to better retain the absorbent pad 80 and isolate the pad 80 and any contents of the pocket 50 from the wearer. FIG. 11 shows the surface of the inner layer 20 and the fluid isolation layer 40 that will face away from the wearer. These are the opposite surfaces from those shown in FIGS. 8A and 8C, FIG. 9A-9D and FIGS. 10A-10D. In the completed product, the attachment bar 46 will form part of the waist strip 64.

The hidden central core pocket 50 will be completed by joining the bottom side 42 and the opposite sides 56 to the face of the inner or anchor layer 20 that will face away from the wearer. The preferable method of attaching the fluid isolation layer 40 to the inner layer 20 would be pocket stitches 58 extending along the periphery of the fluid isolation layer 40. A fluid barrier seam will thus extend around three sides of the fluid isolation layer 40. Multiple stitches may be employed as well as folding the ends of the fluid isolation layer 40 to further seal the pocket 50 and prevent the escape of moisture. The double lines 58 indicating pocket stitches can represent a double stitch line. Alternatively an overlock stitch can be used to form this fluid barrier seam. Overlock stitches employ two threads that overlap or overlock each other, and would thus form a good barrier preventing the passage of moisture. Another option for this fluid barrier seam would be a zig zag stitch. Alternatively the fluid isolation barrier 40 could be attached or joined to the inner layer 20 by sealing the to layers together, for example by heat sealing. Since the width of the fluid isolation layer 40 is less than the distance between the opposite sides 26 of the inner layer 20, as well as the same distance between the opposite sides 16 of the outer layer 10, the sides of the pocket 50 will be inwardly spaced from the curved sides 16 and 20 of the other two layers. The pocket 50 with the fluid isolation layer 40 will then confine moisture and waste so that it will be more difficult for this moisture to reach the sides 16 and 26, which will form leg openings 74 for a diaper 2. The pocket stitches 58, extending through the fluid permeable inner layer 20, will reduce, if not eliminate, lateral flow of moisture within the fluid permeable inner layer 20 by acting as a barrier. Leakage through leg openings 74 will therefore be significantly reduced and in almost all cases will no longer be a problem.

Although the hidden central core pocket 50 can be employed on diapers or other garments 2 that are supplied in different sizes, it is especially useful to employ the hidden central pocket of this invention in a one size fits all diaper. As with conventional one size fits all diapers, male length adjustment fasteners 90 and female length adjustment fasteners 92 can be mounted on the exterior of the outer shell 10. If multiple rows of fasteners of one sex are employed on multiple rows, a fastener of the opposite sex can be attached to fasteners in any row to change the length and thus the size of the master diaper. In this embodiment, three rows of female snap fasteners 92 are used with one row of male snap fasteners 90, so that the make snap fasteners 90 can be snapped into any row of female snap fasteners 92, and this diaper can be adjusted to four different sizes. A one size diaper according to this invention could then be used for infants ranging, for example, from newborn to toddler. As seen in FIGS. 10A-10D, these fasteners 90 and 92 are centrally positioned so that they do not extend beyond the opposite sides 46 of the fluid isolation layer 40 and therefore beyond the lateral edges of the pocket 50. When a fluid absorbent pad 80 is placed in a pocket 50, this pad will be positioned between all of the fasteners 90 and 92 so that the pad will be between the wearer and the snap fasteners 90 and 92. This will provide additional comfort, especially for an infant.

In the preferred embodiment of this invention, the pocket 50 and the fluid isolation layer 40 form the primary barrier to fluid and leakage. The fluid resistant outer layer 10 will serve as a secondary or backup leakage prevention mechanism. This means that leakage around the leg openings 74 will be a less significant problem, and may no longer be necessary to insure that there is a snug fit between the diaper 2 and the wearer's legs. The hidden core pocket 50 is thus particularly suitable for use in a one size fits all or an adjustable size diaper because of the location of the primary moisture barrier inwardly from the leg openings 74, no matter how the size of the diaper 2 is adjusted. Distortion of the leg openings 74 or the lack of a snug fit, as the diaper 2 is adjusted for different sizes, then need not be a problem.

The invention claimed is:

1. An undergarment comprising:
   an outer layer;
   an inner layer;
   a fluid isolation layer between the outer layer and the inner layer, the fluid isolation layer being joined to the inner layer to form a pocket, having a pocket opening on at least one end of the undergarment, wherein:
   the fluid isolation layer has a width less than a distance between opposite sides of the inner layer and outer layer forming leg opening when the garment is positioned on a wearer, so that the pocket is inwardly spaced and isolated from opposite sides of the undergarment leg openings;
   a slot is formed on the inner layer so that slot edges on the inner layer extend around the pocket opening;
   elastic extends completely around the pocket opening and covers a side of the fluid isolation layer overlapping and slot edge; and
   the inner layer comprises a fluid permeable layer.

2. The undergarment of claim 1 wherein the pocket is closed along three sides thereof.

3. The undergarment of claim 2 wherein the a moisture resistant seam joins the fluid isolation layer to the inner layer along three sides thereof with a fourth side of the fluid isolation layer forming an edge of the pocket opening.

4. The undergarment of claim 1 wherein a rear elastic strip is located between the fluid isolation layer and the outer layer and a front elastic strip is located on the inner layer.

5. The undergarment of claim 1 wherein fasteners on the exterior of the outer layer can be attached to alter the size of the undergarment.

6. An undergarment comprising:
an outer layer;
an inner layer;
a fluid isolation layer between the outer layer and the inner layer, the fluid isolation layer being joined to the inner layer to form a pocket, having a pocket opening on at least one end of the undergarment: wherein
the inner layer includes a slot located adjacent one end thereof, the slot in part forming a pocket opening between the inner layer and the fluid isolation layer, and the fluid isolation layer is attached to the inner layer behind the pocket opening formed in part by the slot.

7. The undergarment of claim 6 wherein three sides of the fluid isolation are attached to the inner layer above the slot so that the fluid isolation layer forms an outer layer of the pocket, and the inner layer forms a layer of the pocket adjacent to the skin of the wearer.

8. The undergarment of claim 6 wherein a top edge of the fluid isolation layer and an upper edge of the slot are positioned in overlapping relationship.

9. The undergarment of claim 8 wherein elastic extends over the overlapping top edge of the fluid isolation layer and the upper edge of the slot.

10. The undergarment of claim 9 wherein the elastic extends to opposite sides of the fluid isolation layer.

11. The undergarment of claim 6 wherein the inner layer includes an attachment strip forming the upper edge of the slot.

12. A diaper comprising:
an outer layer defining a diaper length extending between a rear and front end of the diaper;
an inner layer attached to the outer layer;
a fluid isolation layer between the outer layer and the inner layer, the fluid isolation layer being joined to the inner layer to form a pocket for receipt of an absorbent pad, the pocket having a pocket opening on at least one end of the undergarment, wherein the fluid isolation layer has a width less than the outer layer; and
mutually engagable and disengagable length adjustment fasteners arranged in at least three rows and attached to the outer layer, wherein the length of the diaper between the rear and front end of the diaper can be adjusted by engagement of adjustment fasteners in different rows so that the diaper can be adjusted to fit wearers of different sizes, and wherein the pocket extends beyond the rows of adjustment fasteners so that the absorbent pad will be positioned between the adjustment fasteners and the wearer for the wearer's comfort.

13. The diaper of claim 12 wherein the adjustment fasteners comprise male and female snap fasteners.

14. The diaper of claim 13 wherein female fasteners are positioned in at least two rows, and male fasteners are positioned in one row.

* * * * *